(12) United States Patent
Segawa et al.

(10) Patent No.: US 11,684,238 B2
(45) Date of Patent: Jun. 27, 2023

(54) CONTROL DEVICE AND MEDICAL OBSERVATION SYSTEM

(71) Applicant: Sony Olympus Medical Solutions Inc., Tokyo (JP)

(72) Inventors: Kazunori Segawa, Tokyo (JP); Masataka Kado, Tokyo (JP); Hiroshi Ushiroda, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 169 days.

(21) Appl. No.: 17/155,115

(22) Filed: Jan. 22, 2021

(65) Prior Publication Data

US 2021/0290036 A1  Sep. 23, 2021

(30) Foreign Application Priority Data

Mar. 17, 2020 (JP) ................................. 2020-047013

(51) Int. Cl.
*A61B 1/00* (2006.01)
*A61B 1/04* (2006.01)
*A61B 1/06* (2006.01)

(52) U.S. Cl.
CPC .... *A61B 1/00006* (2013.01); *A61B 1/000095* (2022.02); *A61B 1/00188* (2013.01); *A61B 1/043* (2013.01); *A61B 1/0638* (2013.01); *A61B 1/0655* (2022.02); *A61B 1/0661* (2013.01)

(58) Field of Classification Search
CPC ............ A61B 1/00006; A61B 1/00009; A61B 1/000095; A61B 1/043; A61B 1/045; A61B 1/046; A61B 1/05; A61B 1/0638; A61B 1/0655
See application file for complete search history.

(56) References Cited

U.S. PATENT DOCUMENTS

2010/0245550 A1* 9/2010 Ishihara ............... A61B 1/0646
  348/E7.085
2018/0136129 A1* 5/2018 Rizo .................... A61B 5/0071
2020/0305695 A1* 10/2020 Tengeiji ............. G02B 23/2446

FOREIGN PATENT DOCUMENTS

WO  WO-2015012096 A1 * 1/2015 ......... A61B 1/00006

* cited by examiner

*Primary Examiner* — Aaron B Fairchild
*Assistant Examiner* — Julianna J Nicolaus
(74) *Attorney, Agent, or Firm* — Xsensus LLP

(57) ABSTRACT

A control device includes: an acquisition unit configured to acquire first and second image signals generated by an imaging device having an autofocus function by capturing an observation target irradiated with first light and second light having different wavelength bands, respectively; a signal processor configured to detect detection information of the first and second image signals; and a controller configured to calculate a first focal length based on the detection information of the first image signal, calculate a second focal length based on the detection information of the second image signal, and set a focal length of the imaging device to capture the observation target irradiated with the second light to either the first or second focal length at least based on the detection information of the second image signal.

19 Claims, 12 Drawing Sheets

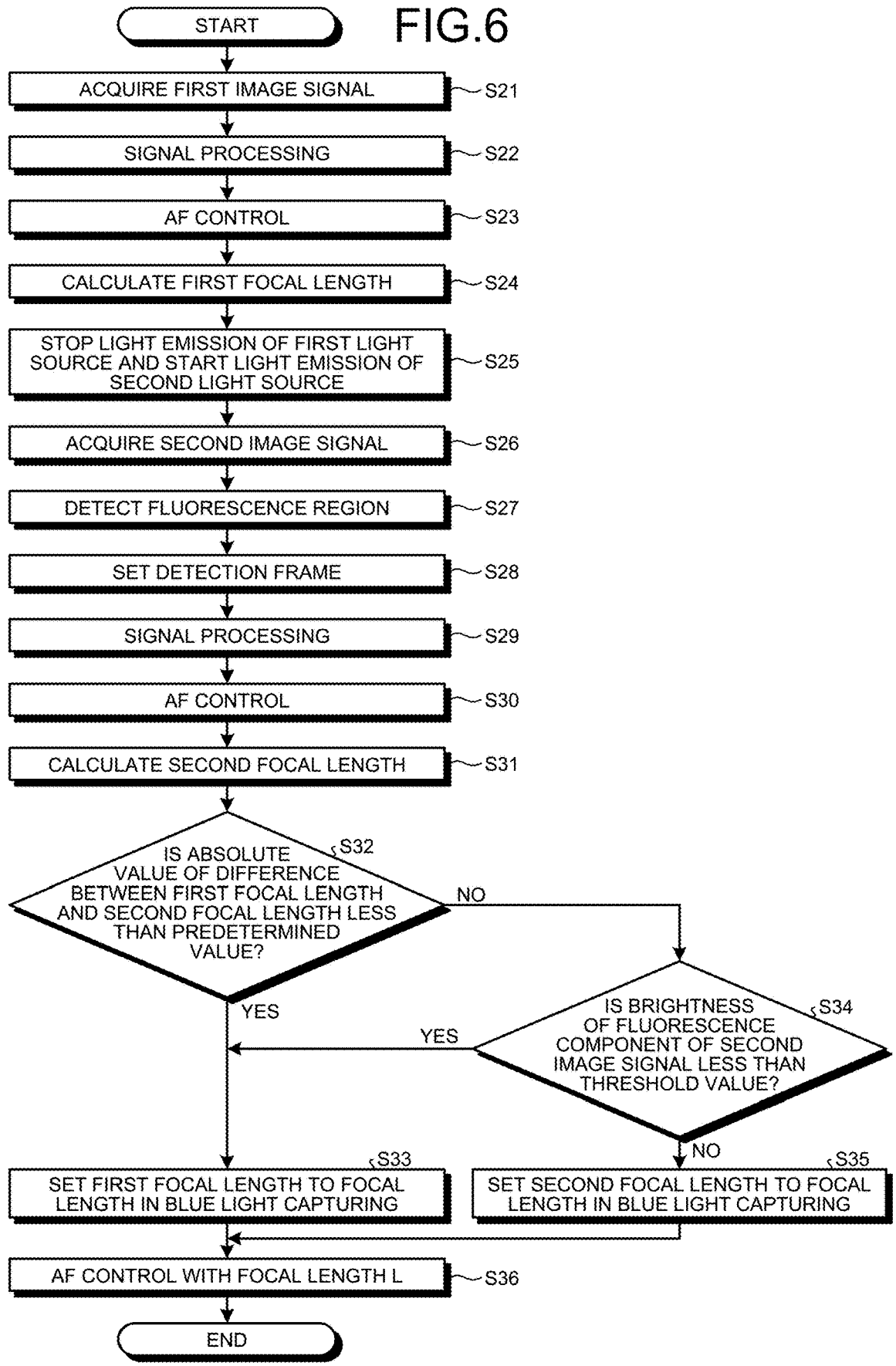

CONTROL DEVICE AND MEDICAL OBSERVATION SYSTEM

CROSS-REFERENCE TO RELATED APPLICATION

This application claims priority from Japanese Application No. 2020-047013, filed on Mar. 17, 2020, the contents of which are incorporated by reference herein in its entirety.

BACKGROUND

The present disclosure relates to a control device and a medical observation system.

A technique for irradiating an observation target with a variety of special light for observation is known (see, for example, JP 2017-131559 A). In this technique, a user such as a doctor observes a subject to be observed by using an image captured by an imaging device having an autofocus function.

SUMMARY

For example, when irradiating fluorescence excitation light as special light and observing fluorescence emitted by a substance included in an observation target, if the brightness of the fluorescence from the observation target is not sufficient, appropriate focusing might not be achieved by autofocus. Therefore, there has been a need for a technique capable of appropriately focusing by autofocus regardless of the observation target.

According to one aspect of the present disclosure, there is provided a control device including: an acquisition unit configured to acquire first and second image signals generated by an imaging device having an autofocus function by capturing an observation target irradiated with first light and second light having different wavelength bands, respectively; a signal processor configured to detect detection information of the first and second image signals; and a controller configured to calculate a first focal length based on the detection information of the first image signal, calculate a second focal length based on the detection information of the second image signal, and set a focal length of the imaging device to capture the observation target irradiated with the second light to either the first or second focal length at least based on the detection information of the second image signal.

BRIEF DESCRIPTION OF THE DRAWINGS

FIG. 6 is a flowchart illustrating an outline of processing performed by a control device according to the second embodiment;

DETAILED DESCRIPTION

Hereinafter, a mode (hereinafter, "embodiment") for carrying out the present disclosure will be described with reference to the accompanying drawings.

First Embodiment

Figure 1:
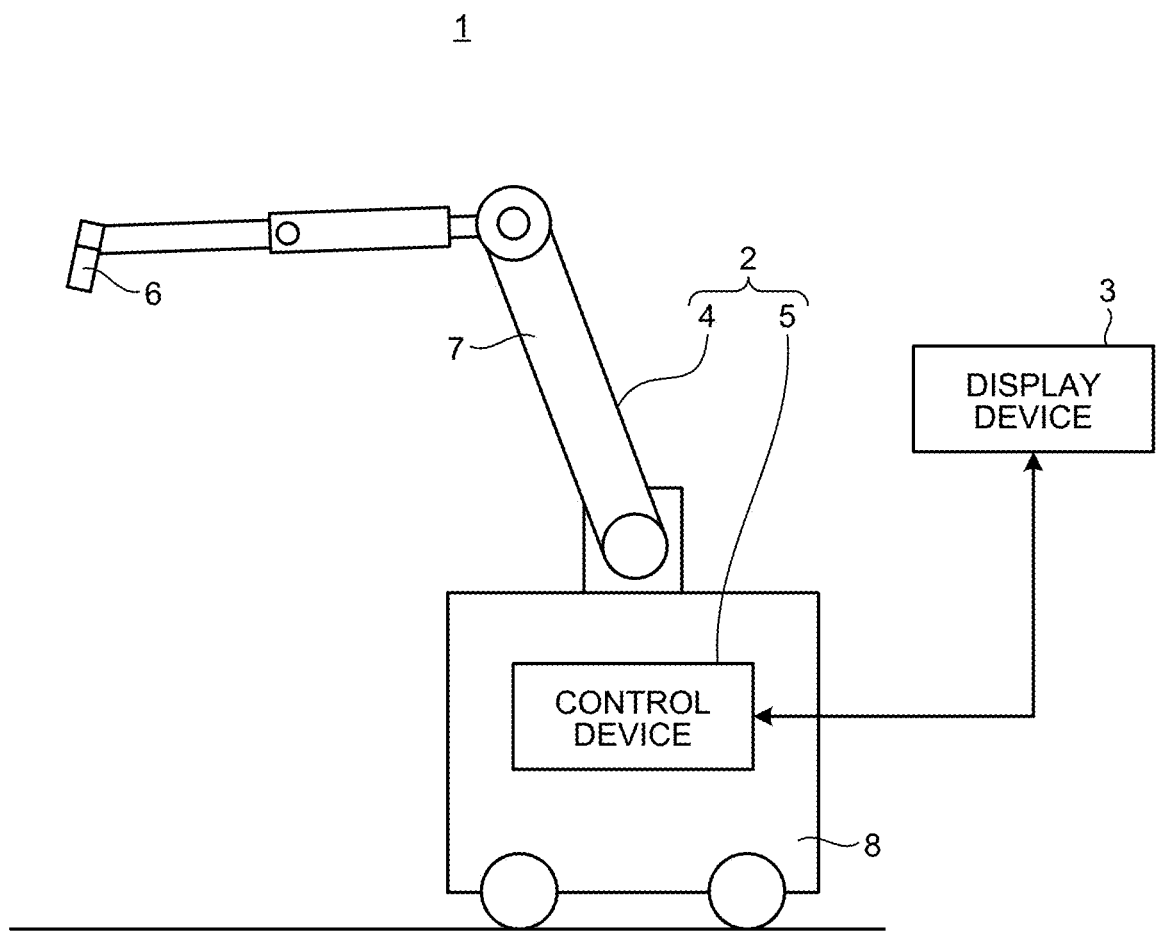
FIG. 1 is a diagram schematically illustrating a medical observation system according to a first embodiment.

FIG. 1 is a diagram schematically illustrating a medical observation system according to a first embodiment. A medical observation system 1 illustrated in FIG. 1 includes a medical observation device 2 and a display device 3.

The medical observation device 2 includes a microscope device 4 and a control device 5. The microscope device 4 has a function as an imaging device that captures an image of an observation target and generates an image signal. The control device 5 has a function as a medical image processing device that performs image processing on the image signal generated by the microscope device 4. The medical observation device 2 according to the present embodiment is a surgical microscope.

The display device 3 receives an image signal for display generated by the control device 5 from the control device 5, and displays an image corresponding to the image signal. The display device 3 is configured by using a display panel made of liquid crystal or organic electro-luminescence (EL).

An appearance configuration of the microscope device 4 will be described. The microscope device 4 includes a microscope unit 6 that captures an image of an observation target, a support 7 that supports the microscope unit 6, and a base 8 that holds a proximal end of the support 7 and incorporates the control device 5.

The microscope unit 6 has a cylindrical unit having a columnar shape. A cover glass is provided on an opening surface at a lower end portion of a main body unit (not illustrated). The cylindrical unit may be grasped by a user, and has a size that allows the user to move the cylindrical unit while grasping the cylindrical unit when changing an imaging field of view of the microscope unit 6. The shape of the cylindrical unit is not limited to the cylindrical shape, and may be a polygonal cylindrical shape.

The support 7 has a plurality of links on an arm unit, and adjacent links are rotatably connected to each other via a joint unit. A transmission cable for transmitting various signals between the microscope unit 6 and the control device 5 and a light guide for transmitting illumination light generated by the control device 5 to the microscope unit 6 pass through a hollow portion formed inside the support 7.

Figure 2:
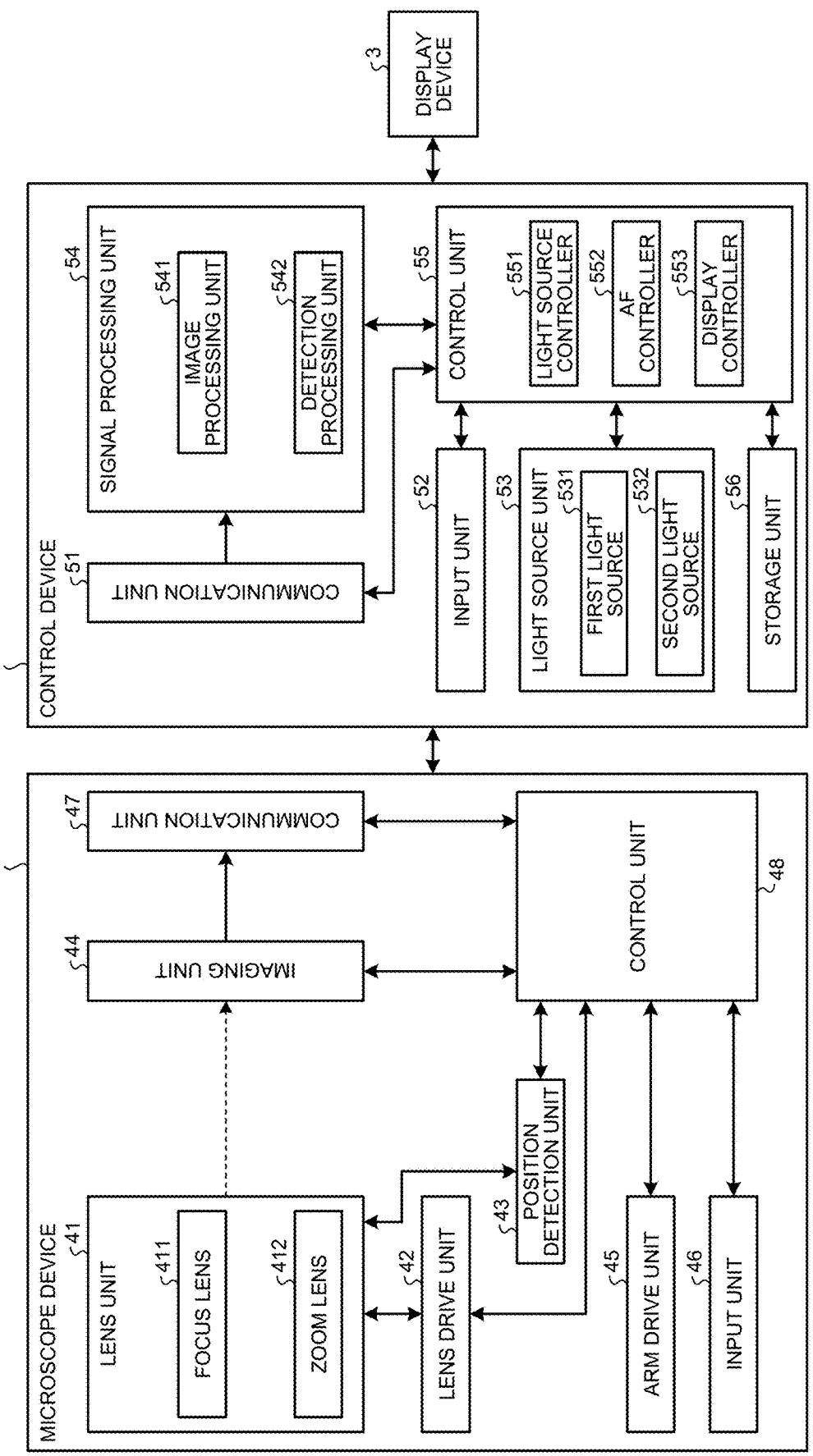
FIG. 2 is a block diagram illustrating a functional configuration of the medical observation system according to the first embodiment.

FIG. 2 is a block diagram illustrating a functional configuration of the medical observation system 1. First, a functional configuration of the microscope device 4 will be described. The microscope device 4 includes a lens unit 41, a lens drive unit 42, a position detection unit 43, an imaging unit 44, an arm drive unit 45, an input unit 46, a communication unit 47, and a control unit 48. The microscope device 4 has an autofocus (AF) function.

The lens unit 41 is configured by using a plurality of lenses that is movable along an optical axis, and forms a condensed subject image on an imaging surface of an imaging element included in the imaging unit 44. The lens unit 41 includes a focus lens 411 for adjusting a focus and a zoom lens 412 for changing an angle of view. The focus lens 411 and the zoom lens 412 are each configured by using one or a plurality of lenses.

The lens drive unit 42 has an actuator for operating the zoom lens and a driver for driving the actuator under the control of the control unit 48.

The position detection unit 43 has two position sensors. The one position sensor detects the position of the focus lens 411 and the other position sensor detects the position of the zoom lens 412. The position detection unit 43 outputs the detected positions of the focus lens 411 and the zoom lens 412 to the control unit 48.

The imaging unit 44 has an imaging element that generates an image signal (analog signal) by forming an image of the subject image condensed by the lens unit 41, and a signal processing unit that performs signal processing such as noise removal or A/D conversion for the image signal (analog signal) from the imaging element. The imaging element is configured by using an image sensor such as a charge coupled device (CCD) or a complementary metal oxide semiconductor (CMOS). Note that the imaging unit 44 may have two imaging elements. In this case, the imaging unit 44 may generate a three-dimensional image (3D image).

Under the control of the control unit 48, the arm drive unit 45 operates the plurality of arms included in the support 7. Specifically, the arm drive unit 45 has an actuator provided at a joint unit between the arms and a driver for driving the actuator.

The input unit 46 receives an input of an operation signal of the microscope device 4 including an AF activation signal. The input unit 46 has a plurality of switches, buttons, or the like provided at positions where the user may operate the microscope unit 6 while grasping the microscope unit 6 on a side surface of the cylindrical unit of the microscope unit 6.

The communication unit 47 is an interface for communicating with the control device 5. The communication unit 47 transmits a digital image signal (RAW signal) generated by the imaging unit 44 to the control device 5, and receives a control signal from the control device 5.

The control unit 48 controls an operation of the microscope device 4 in cooperation with a control unit 55 of the control device 5. The control unit 48 operates the microscope device 4 based on an operation instruction signal that the input unit 46 receives the input, or an operation instruction signal transmitted from the control unit 55 of the control device 5.

The control unit 48 is configured by using at least one processor such as a central processing unit (CPU), a field programmable gate array (FPGA), and an application specific integrated circuit (ASIC).

Next, a functional configuration of the control device 5 will be described. The control device 5 includes a communication unit 51, an input unit 52, a light source unit 53, a signal processing unit 54, the control unit 55, and a storage unit 56. The control device 5 has a function of controlling the AF of the microscope device 4. Note that the AF method may be any of a contrast method, a phase difference method, and an image plane phase difference method.

The communication unit 51 acquires an image signal generated by the microscope device 4 capturing an observation target and transmitted via a transmission cable. The image signal includes information such as a gain adjustment value, a focus lens position, a zoom lens position, a shutter speed, and a diaphragm value at the time of imaging. Hereinafter, an image signal generated in a state in which a first light source 531 of the light source unit 53 emits light is referred to as a first image signal, and an image signal generated in a state in which a second light source 532 of the light source unit 53 emits light is referred to as a second image signal. In this sense, the communication unit 51 has a function as an acquisition unit for acquiring the first and second image signals generated by the microscope device 4. In addition, images corresponding to the first image signal and the second image signal, respectively, are referred to as a first image and a second image.

The input unit 52 receives inputs of various information. The input unit 52 is configured by using a user interface such as a keyboard, a mouse, a touch panel, or a foot switch. Note that the input unit 52 may have at least a part of the functions of the input unit 46 of the microscope device 4.

The light source unit 53 has the first light source 531 and the second light source 532. Light generated by the light source unit 53 is supplied to the microscope device 4 via the light guide, and is irradiated from a distal end thereof toward the observation target.

The first light source 531 is configured with, for example, three light emitting diodes (LEDs) of red, blue, and green, and emits white light as first light.

The second light source 532 emits second light having a wavelength band different from that of the first light. In the first embodiment, the second light source 532 emits narrow band light (hereinafter, referred to as blue light) having a blue component having a center wavelength of 410 nm as the second light. The blue light has a property of emitting red (center wavelength of 630 nm) fluorescence in a case where a substance called PpIX is present in a body of a patient to be observed. PpIX is a substance that is not metabolized and is accumulated in cancer cells as an intermediate product in a case where 5-aminolevulinic acid (5-ALA) is taken up by the cancer cells. On the other hand, it is known that in a case where 5-ALA is taken up by normal tissues, PpIX is metabolized to blood raw material (heme). Therefore, the presence or absence of cancer cells may be diagnosed by irradiating the tissue in which 5-ALA has been taken up with the blue light. Such a diagnostic method is called photodynamic diagnosis (PDD). The second light source 532 is configured by using, for example, an LED or a laser diode (LD).

The signal processing unit 54 performs signal processing on the image signal (RAW signal) acquired by the communication unit 51. In addition, the signal processing unit 54 generates a synchronization signal and a clock of the microscope device 4 and the control device 5. The synchronization signal and the clock generated by the signal processing unit 54 are transmitted to the microscope device 4 via the communication unit 51. The microscope device 4 is driven based on the received synchronization signal and clock. The signal processing unit 54 is configured by using at least one processor such as a CPU, an FPGA, and an ASIC.

The signal processing unit 54 includes an image processing unit 541 and a detection processing unit 542.

The image processing unit 541 generates an image signal for display by performing various image processing, and outputs the generated image signal for display to the display device 3 under the control of the control unit 55. Examples of specific image processing may include known image processing such as gain adjustment, interpolation processing, color correction processing, color enhancement processing, contour enhancement processing, and noise reduction.

The detection processing unit 542 executes detection processing on the image signal for display generated by the image processing unit 541. The detection processing unit 542 detects detection information such as image brightness, contrast, and frequency components within a predetermined detection frame, based on pixel information for each pixel in a detection frame set in a captured image of one frame captured by the imaging unit 44. The detection processing unit 542 outputs the detection information to the control unit 55.

The control unit 55 controls the operation of the control device 5, and integrally controls the operation of the medical observation device 2 in cooperation with the control unit 48 of the microscope device 4. The control unit 55 includes a light source controller 551, an AF controller 552, and a display controller 553.

The light source controller 551 controls the light source unit 53 according to the brightness of the image detected by the detection processing unit 542. In a case where an instruction for capturing an image of blue light is received, or in a case where an AF activation instruction is received, or in a case where movement of the microscope unit 6 including the imaging unit 44 is completed, the light source controller 551 causes the second light source 532 to emit light after continuing the light emission of the first light source 531 for a predetermined time.

The AF controller 552 performs AF control that automatically focuses by transmitting a control signal that brings the position of the focus lens 411 closer to a focusing position based on the detection information detected by the detection processing unit 542 to the control unit 48 of the microscope device 4. The AF controller 552 calculates a focal length using a focusing position of the focus lens 411 detected by the position detection unit 43. Specifically, the AF controller 552 performs the AF control based on an image (RGB image) including all the components of red (R), green (G), and blue (B) to calculate the focal length (first focal length) in the case of an image (first image) captured by irradiating the observation target with white light, and performs the AF control based on an image including only the red component (R component), which is a fluorescence component to calculate the focal length (second focal length) in the case of an image (second image/blue light image) captured by irradiating the observation target with blue light.

Subsequently, the AF controller 552 compares a first focal length (L1) and a second focal length (L2), and sets a focal length in blue light capturing according to the comparison result. The AF controller 552 sets the focal length in the following three cases.

1. In a case where an absolute value |L1−L2| of a difference between the two focal lengths is smaller than a predetermined value ΔL (|L1−L2|<ΔL), the first focal length L1 is adopted.

2. In a case where the absolute value |L1−L2| of the difference between the two focal lengths is equal to or greater than the predetermined value ΔL (|L1−L2|≥ΔL), and a brightness B of a fluorescence component of the second image is smaller than a threshold value Th (B<Th), the first focal length L1 is adopted.

3. In a case where the difference between the two focal lengths is equal to or greater than the predetermined value and the brightness B of the fluorescence component of the second image is equal to or greater than the threshold value Th (B≥Th), the second focal length L2 is adopted.

Note that in a case where the AF controller 552 performs the determination, an average of a plurality of first focal lengths calculated at a predetermined sampling interval may be compared with an average of a plurality of second focal lengths, or the focal lengths of the representative images defined by a predetermined rule may be compared.

Thereafter, the AF controller 552 performs AF control for transmitting a control signal for adjusting the position of the focus lens 411 according to the focal length set by the determination to the control unit 48 of the microscope device 4.

The display controller 553 controls the display on the display device 3. In a case where the microscope device 4 performs blue light capturing, the display controller 553 causes the display device 3 to display a message such as "blue light capturing on". As a result, the user may visually grasp on the display screen of the display device 3 that the blue light capturing is on, that is, the imaging unit 44 is generating the second image signal.

The control unit 55 is configured by using at least one processor such as a CPU, an FPGA, and an ASIC. The signal processing unit 54 and the control unit 55 may be configured by using a common processor.

The storage unit 56 stores various programs for operating the control device 5 at the position of the zoom lens 412, and temporarily stores data being processed by the control device 5. The storage unit 56 is configured by using a read only memory (ROM), a random access memory (RAM), or the like.

Figure 3:
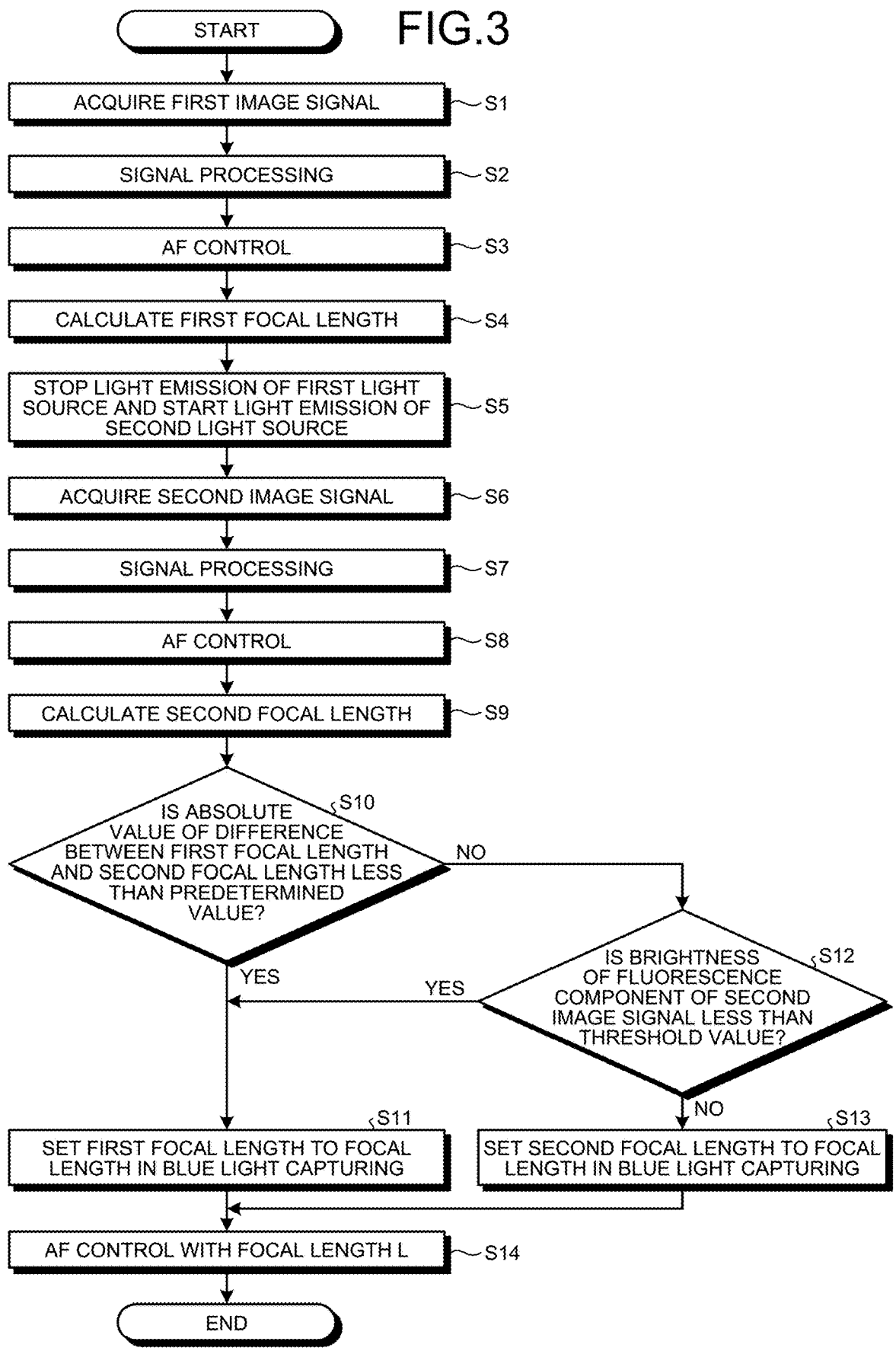
FIG. 3 is a flowchart illustrating an outline of processing performed by a control device according to the first embodiment.

FIG. 3 is a flowchart illustrating an outline of the processing performed by the control device 5, and is a flowchart illustrating an outline of the processing performed in a case where the input unit 46 receives an instruction for blue light capturing, or in a case where the input unit 46 receives an AF (one-shot AF) activation instruction, or in a case where the movement of the microscope unit 6 including the imaging unit 44 is completed. In FIG. 3, it is assumed that the first light source 531 emits white light at the time of starting a series of processing.

If the communication unit 51 acquires the first image signal (step S1), the signal processing unit 54 performs signal processing on the first image signal (step S2). Specifically, the image processing unit 541 generates the first image signal for display, and the detection processing unit 542 detects detection information in a detection frame of the first image signal for display and outputs the detection information to the control unit 55.

Subsequently, the AF controller 552 performs AF control based on the detection information acquired from the signal processing unit 54 (step S3), and calculates the first focal length L1 (step S4).

Thereafter, the light source controller 551 stops the light emission of the first light source 531 and starts the light emission of the second light source 532 (step S5). As a result, the observation target begins to be irradiated with blue light.

After step S5, in a case where the communication unit 51 acquires the second image signal (step S6), the signal processing unit 54 performs signal processing on the second image signal (step S7). In step S7, the image processing unit 541 generates a second image signal for display, and the detection processing unit 542 detects detection information of an R component in a detection frame of the second image signal for display and outputs the detection information to the control unit 55.

Subsequently, the AF controller 552 performs AF control based on the detection information acquired from the signal processing unit 54 (step S8), and calculates the second focal length L2 (step S9).

Thereafter, the AF controller 552 sets the focal length for performing AF (steps S10 to S13). First, the AF controller 552 calculates an absolute value |L1−L2| of a difference between the first focal length L1 and the second focal length L2 and compares the absolute value |L1−L2| with a predetermined value ΔL (step S10). As a result of the comparison, in a case where |L1−L2|<ΔL (step S10: Yes), the AF controller 552 sets the first focal length L1 to the focal length L in blue light capturing (step S11).

On the other hand, as a result of the comparison in step S10, in a case where |L1−L2|≥ΔL (step S10: No), the AF controller 552 compares the brightness B of the R component in the detection frame of the second image signal with the threshold value Th (step S12). In a case where B<Th (step S12: Yes), the AF controller 552 shifts to step S11. On the other hand, in a case where B≥Th (step S12: No), the AF controller 552 sets the second focal length L2 to the focal length L in blue light capturing (step S13).

After step S11 or S13, the AF controller 552 performs AF control with the focal length L (step S14). Specifically, the AF controller 552 transmits a control signal for adjusting the position of the focus lens 411 to the control unit 48 of the microscope device 4 based on the determination result in step S9. Thereafter, the control device 5 ends a series of processing.

Note that in a case where the AF controller 552 sets the focal length, the brightness B of the R component in the detection frame of the second image signal is first compared with the threshold value Th without performing the processing of step S10 described above, and the focal length L in blue light capturing may be set according to the comparison result. As a result, the processing of the control device 5 may be simplified.

According to the first embodiment described above, since the first focal length is calculated based on the detection information of the first image signal, the second focal length is calculated based on the detection information of the second image signal, and the focal length of the imaging device to capture an image is set to either the first or second focal length based on at least the detection information of the second image signal, focusing by autofocus may be appropriately performed regardless of the observation target by using a more preferable focal length.

In addition, according to the first embodiment, since the focal length for acquiring the second image signal is set to the first focal length in a case where the absolute value of the difference between the first focal length and the second focal length is smaller than the predetermined value, and the focal length for acquiring the second image signal is set to either the first or second focal length according to the comparison result between the brightness of the red component of the second image signal and the threshold value in a case where the absolute value of the difference between the first focal length and the second focal length is equal to or greater than the predetermined value, by setting the focal length of the first image signal in a case where the second image signal is dark, the user may perform medical treatment such as surgery by viewing an image with good visibility.

Second Embodiment

Figure 4:
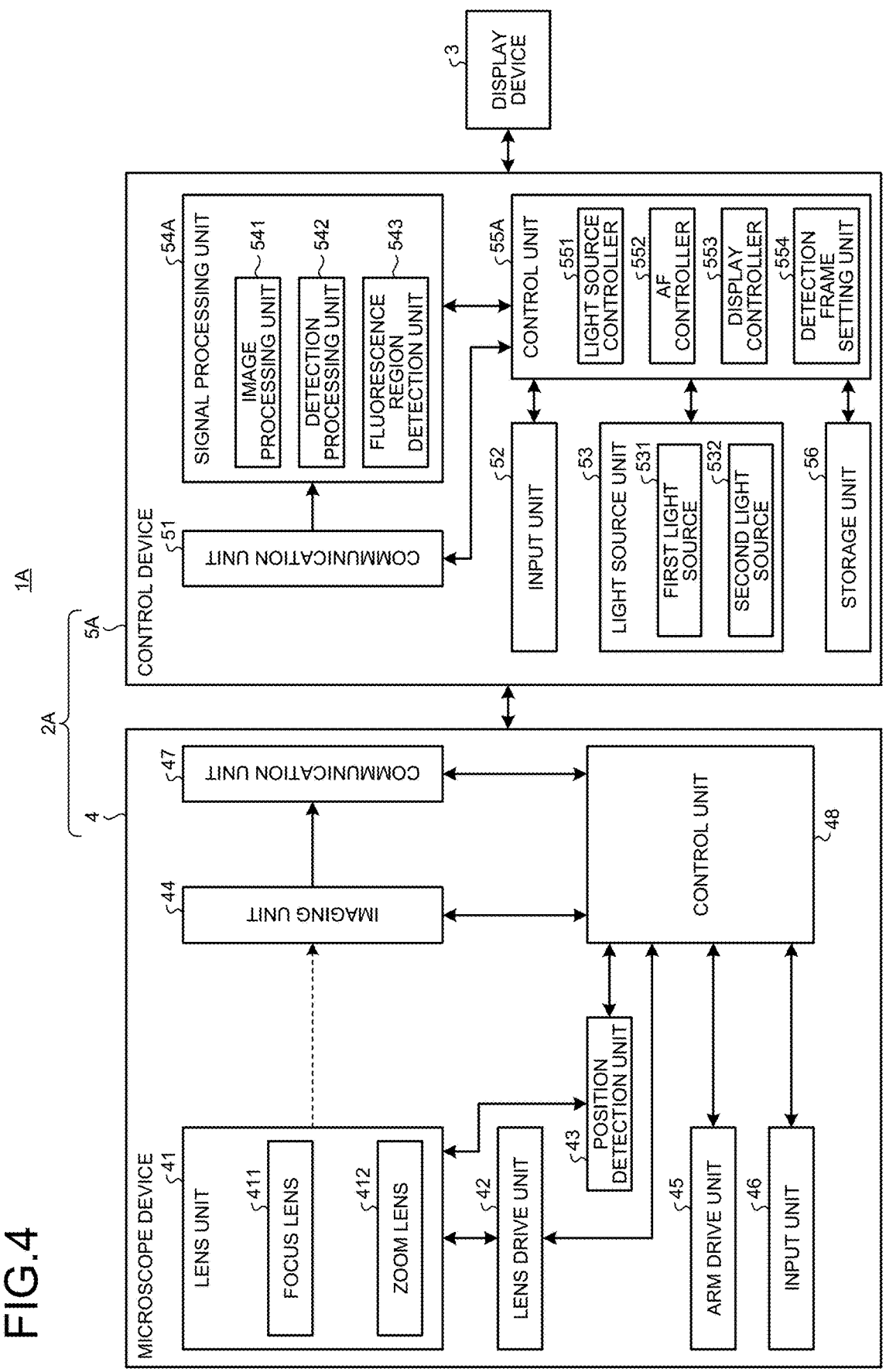
FIG. 4 is a block diagram illustrating a functional configuration of a medical observation system according to a second embodiment.

FIG. 4 is a block diagram illustrating a functional configuration of a medical observation system according to a second embodiment. In FIG. 4, the same reference numerals are given to the portions having the same functional configuration as the medical observation system 1 described in the first embodiment.

A medical observation system 1A illustrated in FIG. 4 includes a medical observation device 2A and the display device 3. The medical observation device 2A includes the microscope device 4 and a control device 5A.

A functional configuration of the control device 5A will be described below. The control device 5A is different from the control device 5 described in the first embodiment in the functional configurations of the signal processing unit and the control unit.

A signal processing unit 54A includes an image processing unit 541, a detection processing unit 542, and a fluorescence region detection unit 543. The fluorescence region detection unit 543 detects a fluorescence region in which fluorescence (R component) is emitted in the second image signal generated by blue light capturing, generates information (fluorescence region information) such as a pixel position for specifying the fluorescence region, and outputs the information to a control unit 55A.

The control unit 55A includes a light source controller 551, an AF controller 552, a display controller 553, and a detection frame setting unit 554. The detection frame setting unit 554 sets a detection frame based on the fluorescence region information generated by the fluorescence region detection unit 543. The detection frame setting unit 554 sets the detection frame so that a ratio of an area of the fluorescence region included in the detection frame to the area of the fluorescence region is equal to or greater than a predetermined threshold value.

Figure 5A:
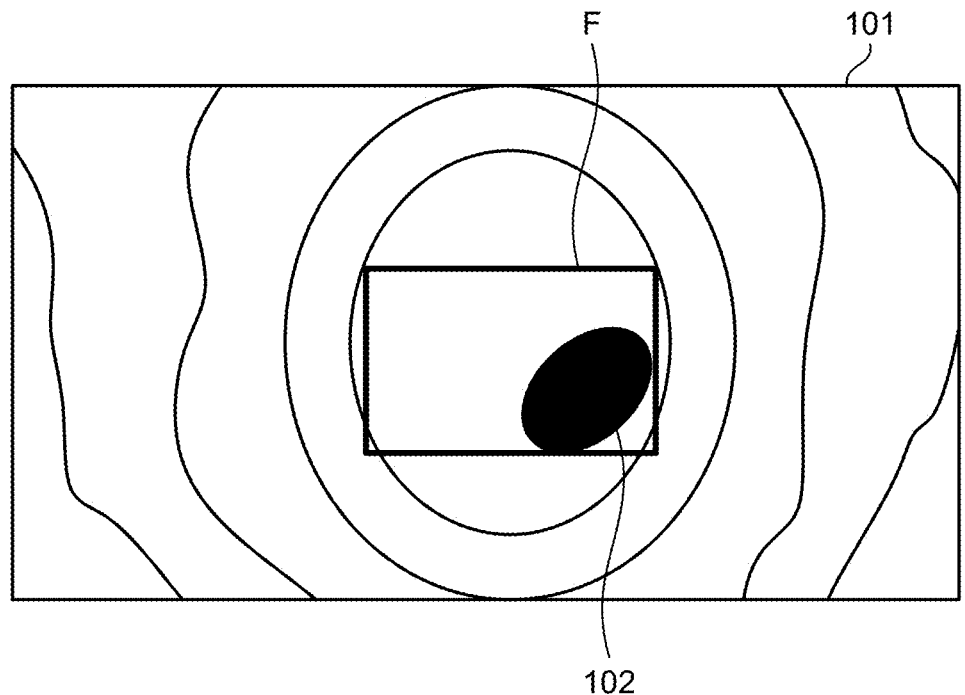
FIG. 5A is a diagram (Part 1) schematically illustrating an outline of processing of a fluorescence region detection unit and a detection frame setting unit.
Figure 5B:
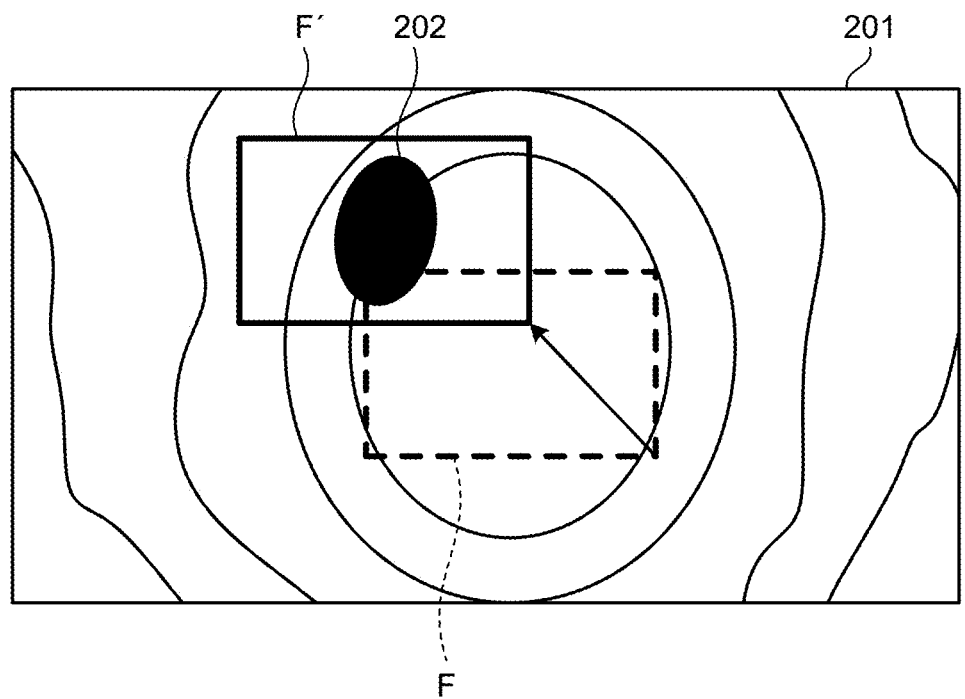
FIG. 5B is a diagram (Part 2) schematically illustrating an outline of processing of a fluorescence region detection unit and a detection frame setting unit.

FIGS. 5A and 5B are diagrams schematically illustrating an outline of processing of the fluorescence region detection unit 543 and the detection frame setting unit 554. An observation image 101 illustrated in FIG. 5A schematically illustrate an image in which the subject is recessed toward a back side of a paper surface in a central portion of a screen, and a fluorescence region 102 is located substantially in the central portion. The fluorescence region 102 is located inside a preset detection frame F. In this case, in a case where the fluorescence region detection unit 543 detects the fluorescence region 102 and generates fluorescence region information, the detection frame setting unit 554 determines that the fluorescence region 102 exists inside the detection frame F based on the fluorescence region information, and does not move the detection frame.

On the other hand, in an observation image 201 illustrated in FIG. 5B, a fluorescence region 202 is located substantially in an upper left of the central portion of the screen. For comparison, like the observation image 101, the observation image 201 schematically illustrates an image in which the subject is recessed toward the back side of the paper surface in the central portion of the screen. Such a fluorescence region 202 is only partially included in the preset detection frame F (indicated by a broken line). In this case, in a case where the fluorescence region detection unit 543 detects the fluorescence region 202 and generates the fluorescence region information, the detection frame setting unit 554 determines that the fluorescence region 202 does not exist inside the detection frame F based on the fluorescence region information, moves the detection frame, and moves the detection frame to a position where the fluorescence region 202 fits within the frame. FIG. 5B illustrates a state in which the fluorescence region 202 is contained inside a detection frame F' after movement.

FIG. 6 is a flowchart illustrating an outline of the processing performed by the control device 5A, and is a flowchart illustrating an outline of the processing performed in a case where the input unit 46 receives an instruction for blue light capturing, or in a case where the input unit 46 receives an AF activation instruction, or in a case where the movement of the microscope unit 6 is completed. In FIG. 6, as in FIG. 3, it is assumed that the first light source 531 emits white light at the time of starting a series of processing.

First, the processing of steps S21 to S26 sequentially corresponds to the processing of steps S1 to S6 described above.

In step S27, the fluorescence region detection unit 543 detects the fluorescence region using the second image signal acquired in step S26, generates the fluorescence region information, and outputs the fluorescence region information to the control unit 55A (step S27).

Thereafter, the detection frame setting unit 554 sets the detection frame with reference to the fluorescence region information (step S28).

The subsequent processing of steps S29 to S36 corresponds sequentially to the processing of steps S7 to S14 described above. Note that a predetermined value in step S32 and a threshold value in step S34 do not have to be the same values as in the first embodiment.

Note that in the second embodiment, in a case where the AF controller 552 sets the focal length, without performing the comparison processing (step S32) between the absolute value |L1−L2| of the difference between the first focal length L1 and the second focal length L2 and the predetermined value ΔL, the brightness B of the R component in the detection frame of the second image signal may be compared with the threshold value Th, and the focal length L in blue light capturing may be set according to the comparison result.

According to the second embodiment described above, as in the first embodiment, focusing by autofocus may be appropriately performed regardless of the observation target, and the user may perform medical treatment while viewing an image with good visibility.

In addition, according to the second embodiment, since the detection frame is set according to the detection result of the fluorescence region, it is possible to perform appropriate focusing according to the captured subject image.

Note that instead of the control device 5A automatically setting the detection frame, the user may be able to manually set the detection frame via the input unit 46 or the input unit 52 by viewing the image. In addition, the automatic setting and the manual setting of the detection frame may be selectively switched. The fluorescence region detection unit 543 is not required in a case where only the manual setting of the detection frame is possible.

Third Embodiment

Figure 7:
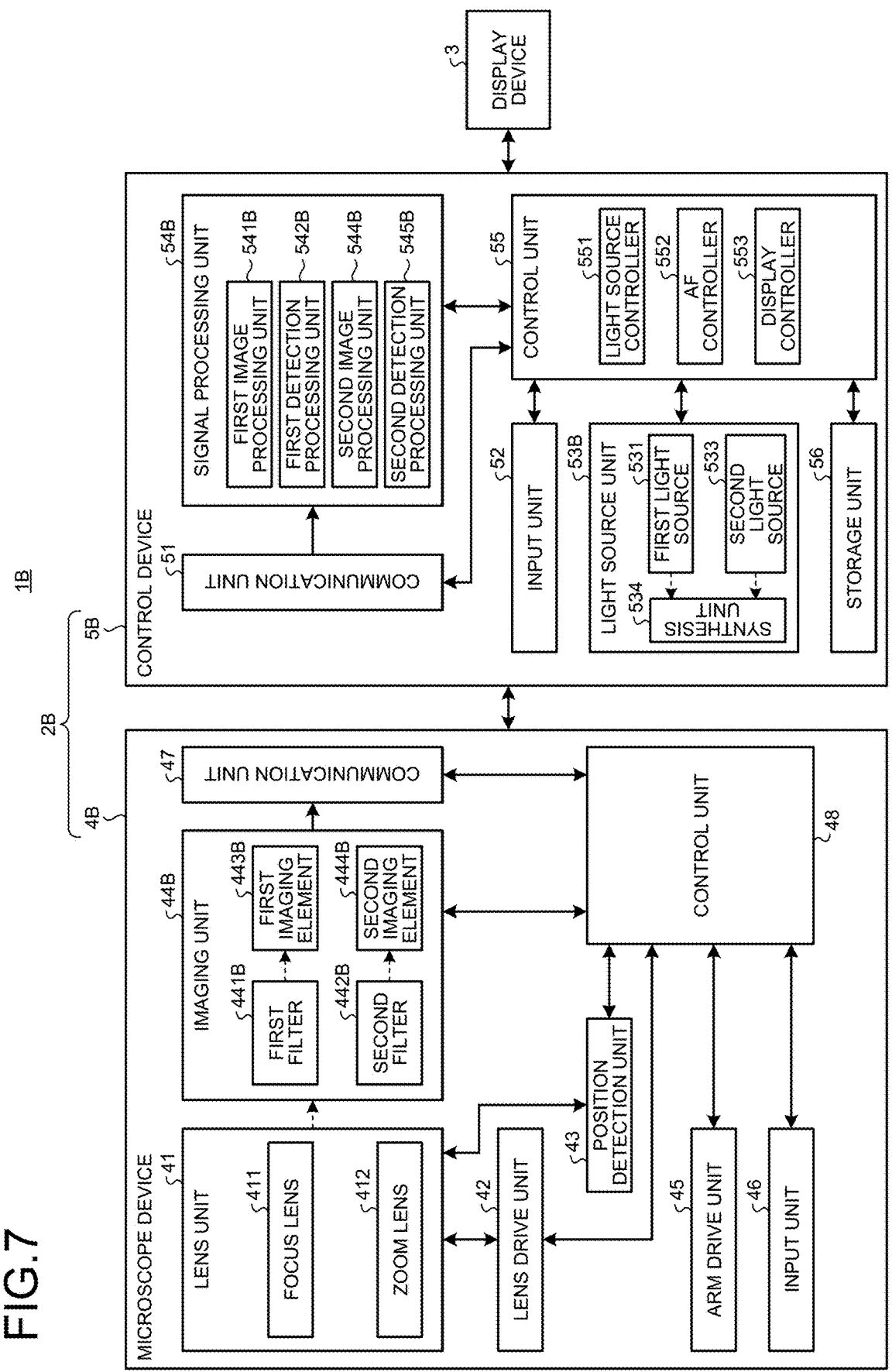
FIG. 7 is a block diagram illustrating a functional configuration of a medical observation system according to a third embodiment.

FIG. 7 is a block diagram illustrating a functional configuration of a medical observation system according to a third embodiment. In FIG. 7, the same reference numerals are given to the portions having the same functional configuration as the medical observation system 1 described in the first embodiment.

A medical observation system 1B illustrated in FIG. 7 includes a medical observation device 2B and the display device 3. The medical observation device 2B includes a microscope device 4B and a control device 5B.

First, the control device 5B will be described. The control device 5B includes the communication unit 51, the input unit 52, a light source unit 53B, a signal processing unit 54B, and the control unit 55.

The light source unit 53B includes the first light source 531, a second light source 533, and a synthesis unit 534. The second light source 533 emits infrared light in a narrow band having a center wavelength of around 774 nm. Such infrared light has a property as excitation light that excites indocyanine green (ICG) to emit fluorescence having a center wavelength of around 805 nm. The second light source 533 is provided for diagnosing the presence or absence of blood flow by injecting ICG into the body of the patient to be observed, irradiating the body with infrared light, and observing fluorescence. Such a diagnostic method is called infrared imaging (IRI). The second light source 532 is configured by using, for example, an LED or a laser diode (LD).

The synthesis unit 534 synthesizes the white light emitted by the first light source 531 and the infrared light emitted by the second light source 533, and supplies the synthesized illumination light to the microscope device 4B. The synthesis unit 534 is configured by using a prism and a lens. As a result, in a case where the first light source 531 and the second light source 533 emit light at the same time, the observation target may be simultaneously irradiated with the white light and the infrared light.

The signal processing unit 54B includes a first image processing unit 541B, a first detection processing unit 542B, a second image processing unit 544B, and a second detection processing unit 545B. The first image processing unit 541B and the first detection processing unit 542B perform signal processing on the first image signal acquired by the communication unit 51. In addition, the second image processing unit 544B and the second detection processing unit 545B perform signal processing on the second image signal acquired by the communication unit 51.

The first image processing unit 541B generates a first image signal for display by performing the same image processing as the image processing unit 541 on the first image signal. The first detection processing unit 542B performs the same detection processing as the detection processing unit 542 on the first image signal, and outputs the detection information of the first image (white light image) to the control unit 55.

The second image processing unit 544B generates a second image signal for display by performing the same image processing as the image processing unit 541 on the second image signal. Note that the second image processing unit 544B may generate a second image signal for display by performing processing of superimposing a predetermined color component on the fluorescence component.

The second detection processing unit 545B performs the same detection processing as the detection processing unit 542 on the second image signal. The second detection processing unit 545B performs the same detection processing as the detection processing unit 542 on the second image signal, and outputs the detection information of the second image (fluorescence image) to the control unit 55.

The light source controller 551 of the control unit 55 switches between a mode in which only the first light source 531 emits light and a mode in which the first light source 531 and the second light source 533 emit light at the same time according to the operation signal received by the input unit 46.

Next, the microscope device 4B will be described. The microscope device 4B differs from the imaging unit 44 of the microscope device 4 described above in a functional configuration of an imaging unit 44B. The imaging unit 44B includes a first filter 441B, a second filter 442B, a first imaging element 443B, and a second imaging element 444B.

Figure 8:
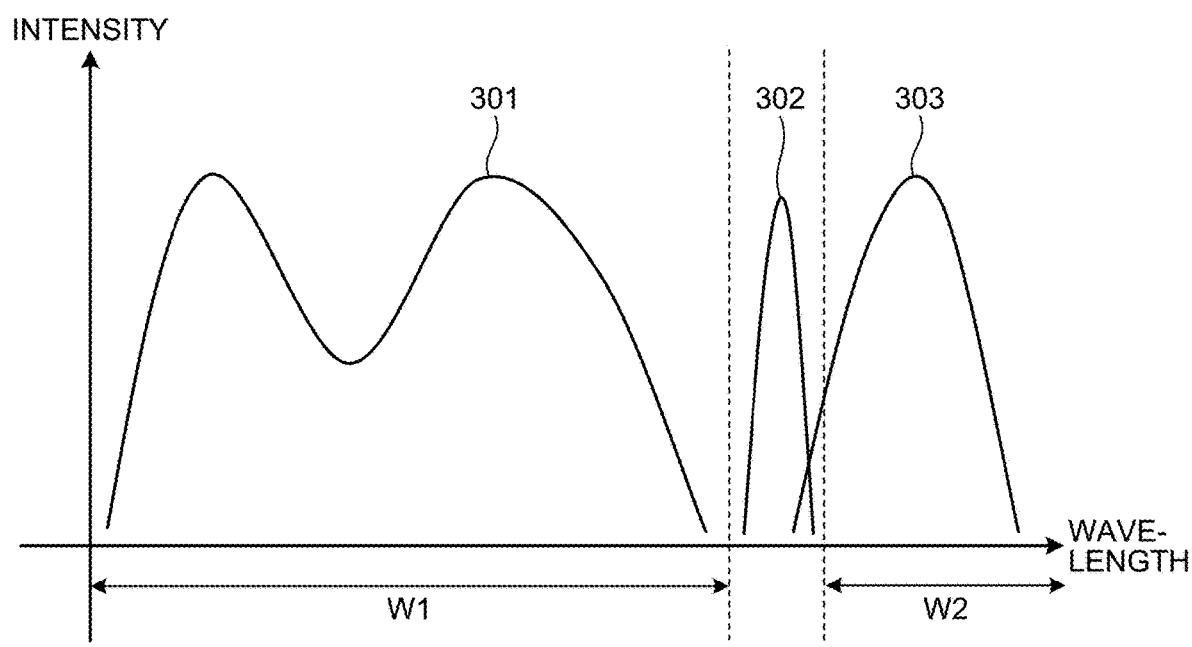
FIG. 8 is a diagram schematically illustrating transmission characteristics of a first filter and a second filter.

FIG. 8 is a diagram schematically illustrating transmission characteristics of the first filter 441B and the second filter 442B. In FIG. 8, a horizontal axis is a wavelength and a vertical axis is an intensity. A curve 301 illustrates a spectrum of white light, a curve 302 illustrates a spectrum of infrared light, and a curve 303 illustrates a spectrum of fluorescence. A wavelength band W1 illustrates a wavelength band transmitted by the first filter 441B. In addition, a wavelength band W2 illustrates a wavelength band transmitted by the second filter 442B. As is clear from FIG. 8, the first filter 441B transmits only white light and cuts infrared light and fluorescence. On the other hand, the second filter 442B transmits only fluorescence and cuts white light and infrared light. Note that the second filter 442B may be configured by using two filters, a filter that cuts white light and a filter that cuts infrared light.

The first imaging element 443B forms an image of the white light transmitted through the first filter 441B to generate a first image signal. In addition, the second imaging element 444B forms an image of the fluorescence transmitted through the second filter 442B to generate a second image signal. Note that instead of providing the first filter 441B and the second filter 442B, the first imaging element 443B may be provided with a color filter having the same transmission characteristics as the first filter 441B, while the second imaging element 444B may be provided with a color filter having the same transmission characteristics as the second filter 442B.

Figure 9:
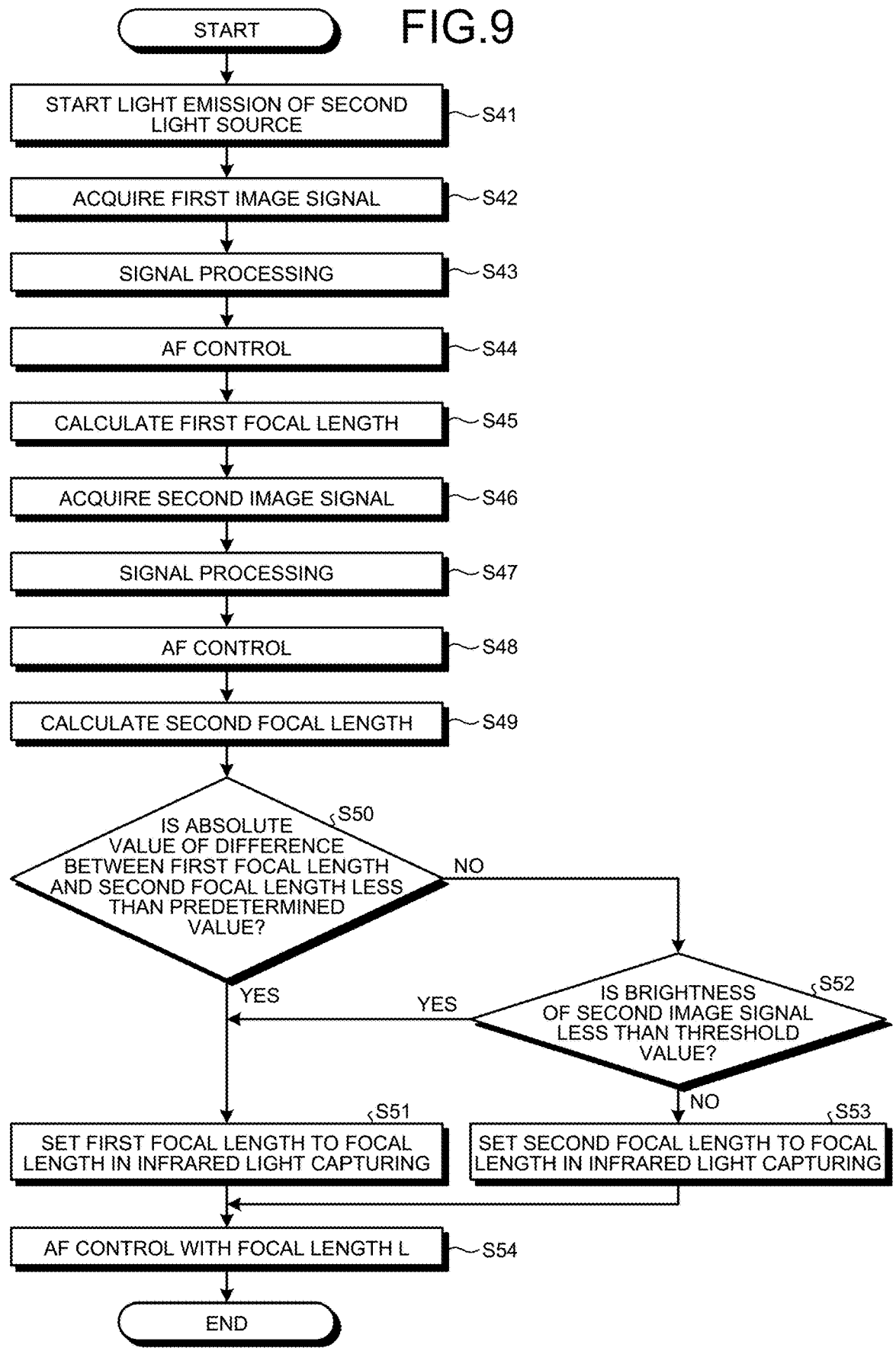
FIG. 9 is a flowchart illustrating an outline of processing performed by a control device according to a third embodiment.

FIG. 9 is a flowchart illustrating an outline of the processing performed by the control device 5B, and is a flowchart illustrating an outline of the processing performed in a case where the input unit 46 receives an instruction for infrared light capturing, or in a case where the input unit 46 receives an AF activation instruction, or in a case where the movement of the imaging unit 44B including the imaging unit 44 is completed. In FIG. 9, it is also assumed that the first light source 531 emits white light at the time of starting a series of processing.

First, the light source controller 551 starts the issue of the second light source 533 while the first light source 531 is emitting light (step S41). As a result, white light and infrared light are simultaneously irradiated to the observation target, and the first imaging element 443B and the second imaging element 444B generate the first image signal and the second image signal in parallel, respectively.

Thereafter, the processing from the acquisition of the first image signal by the communication unit 51 (step S42) to the calculation of the first focal length L1 by the AF controller 552 (step S45) sequentially corresponds to the processing of steps S1 to S4 described in the first embodiment.

In addition, the processing from the acquisition of the second image signal by the communication unit 51 (step S46) to the calculation of the second focal length L2 by the AF controller 552 (step S49) sequentially corresponds to the processing of steps S6 to S9 described in the first embodiment.

The processing (steps S50 to S54) for setting the focal length L after step S49 sequentially corresponds to the processing of steps S10 to S14 described in the first embodiment. However, in step S52, the AF controller 552 compares the brightness in the detection frame of the second image signal with a predetermined threshold value. In addition, in step S51 and step S53, the AF controller 552 sets the focal length in infrared light capturing. Note that a predetermined value in step S50 and a threshold value in step S52 do not have to be the same values as in the first embodiment.

Note that the processing of steps S46 to S49 may be performed before the processing of steps S42 to S45. In addition, the processing of steps S42 to S45 and the processing of steps S46 to S49 may be performed in parallel. In addition, also in the third embodiment, in a case where the AF controller 552 sets the focal length, without performing the comparison processing (step S50) between the absolute value |L1−L2| of the difference between the first focal length L1 and the second focal length L2 and the predetermined value ΔL, the brightness B in the detection frame of the second image signal may be compared with the threshold value Th, and the focal length L in infrared light capturing may be set according to the comparison result.

According to the third embodiment described above, even in a case where irradiating white light and infrared light at the same time, focusing by autofocus may be appropriately performed regardless of the observation target as in the first embodiment.

In addition, according to the third embodiment, since the focal length for acquiring the second image signal is set to the first focal length in a case where the absolute value of the difference between the first focal length and the second focal length is smaller than the predetermined value, and the focal length for acquiring the second image signal is set to either the first or second focal length according to the comparison result between the brightness of the second image signal and the threshold value in a case where the absolute value of the difference between the first focal length and the second focal length is equal to or greater than the predetermined value, by setting the focal length of the first image signal in a case where the second image signal is dark, the user may perform medical treatment such as surgery by viewing an image with good visibility.

Note that also in the third embodiment, as in the second embodiment described above, the control device may have a function of automatically or manually setting and changing the detection frame according to the image.

Fourth Embodiment

Figure 10:
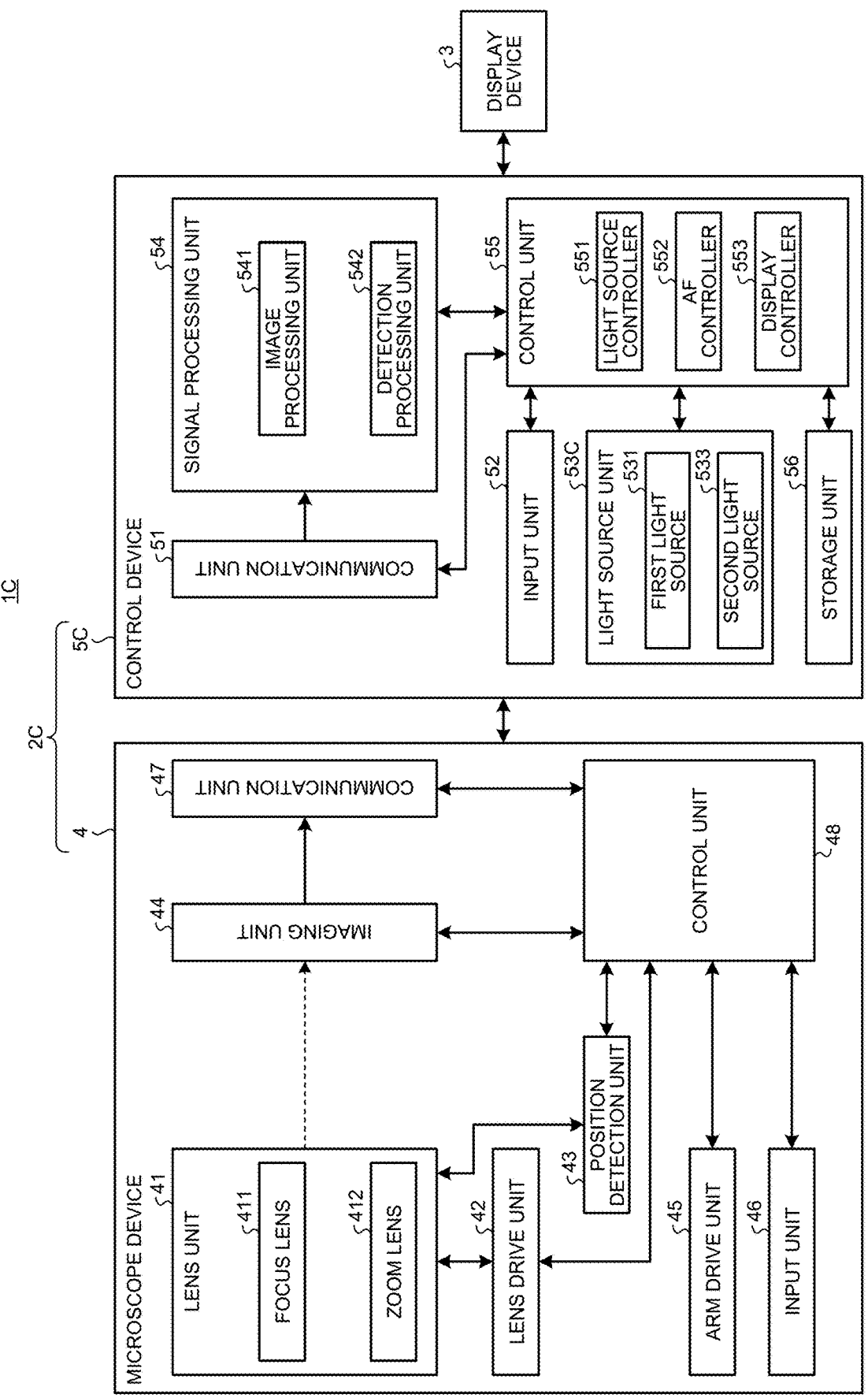
FIG. 10 is a block diagram illustrating a functional configuration of a medical observation system according to a fourth embodiment.

FIG. 10 is a block diagram illustrating a functional configuration of a medical observation system according to a fourth embodiment. In FIG. 10, the same reference numerals are given to the portions having the same functional configurations as the medical observation system 1 described in the first embodiment and the medical observation system 1B described in the third embodiment.

A medical observation system 1C illustrated in FIG. 7 includes a medical observation device 2C and the display device 3. The medical observation device 2C includes a microscope device 4C and a control device 5C.

The control device 5C includes the communication unit 51, the input unit 52, a light source unit 53C, the signal processing unit 54, and the control unit 55. The light source unit 53C has the first light source 531 and the second light source 533. In the fourth embodiment, the first light source 531 and the second light source 533 emit white light and infrared light alternately in a time-division manner under the control of the light source controller 551 when performing infrared light capturing.

Figure 11:
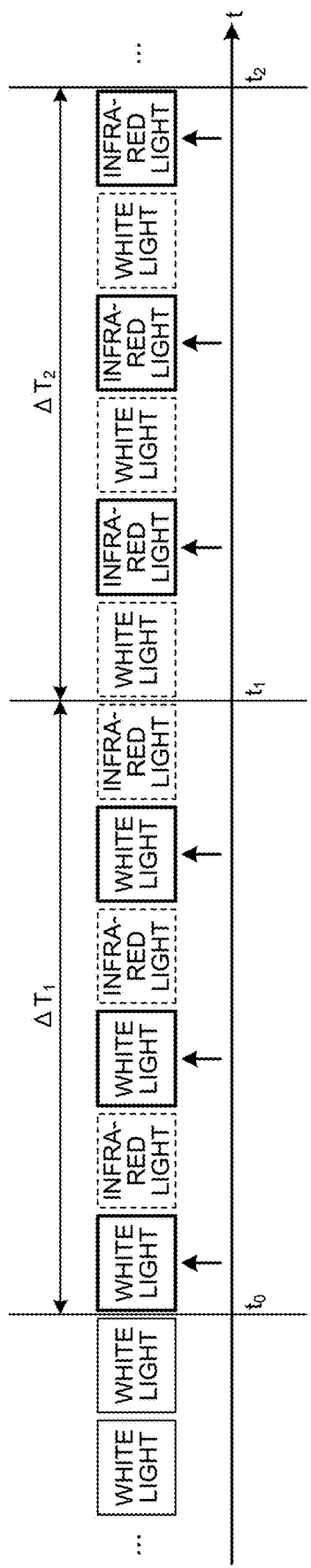
FIG. 11 is a diagram for explaining an outline of processing performed by a control device according to the fourth embodiment.

FIG. 11 is a diagram illustrating an outline of processing performed by the control device 5C. In a case where the input unit 46 receives an operation to turn on infrared light capturing at time $t_0$ in FIG. 11, the light source controller 551 controls the first light source 531 and the second light source 533 to alternately emit light in a time-division manner. In a first time zone $\Delta T_1$ from immediately after the start of infrared light capturing to the time $t_1$, the AF controller 552 calculates only a focal length of a white light image. On the other hand, in a second time zone $\Delta T_2$ from the time $t_1$ to the time $t_2$, the AF controller 552 calculates only a focal length of an infrared light image. In FIG. 11, a frame of the image for which the focal length is calculated is indicated by a solid line and indicated by an upward arrow, and a frame for which the focal length is not calculated is indicated by a broken line. The first time zone $\Delta T_1$ and the second time zone $\Delta T_2$ are only required to each include one or more frames of the image to be calculated for the focal length, and the lengths of the time zones may be different from each other. In addition, the light emission order of the first light source 531 and the second light source 533 after the start of infrared light capturing may be reversed.

Thereafter, the AF controller 552 obtains an average focal length of the white light image calculated in the first time zone $\Delta T_1$ and the average focal length of the infrared light image calculated in the second time zone $\Delta T_2$, and sets the focal length in infrared light capturing by performing the same comparison as in the first embodiment with respect to these averages.

Figure 12:
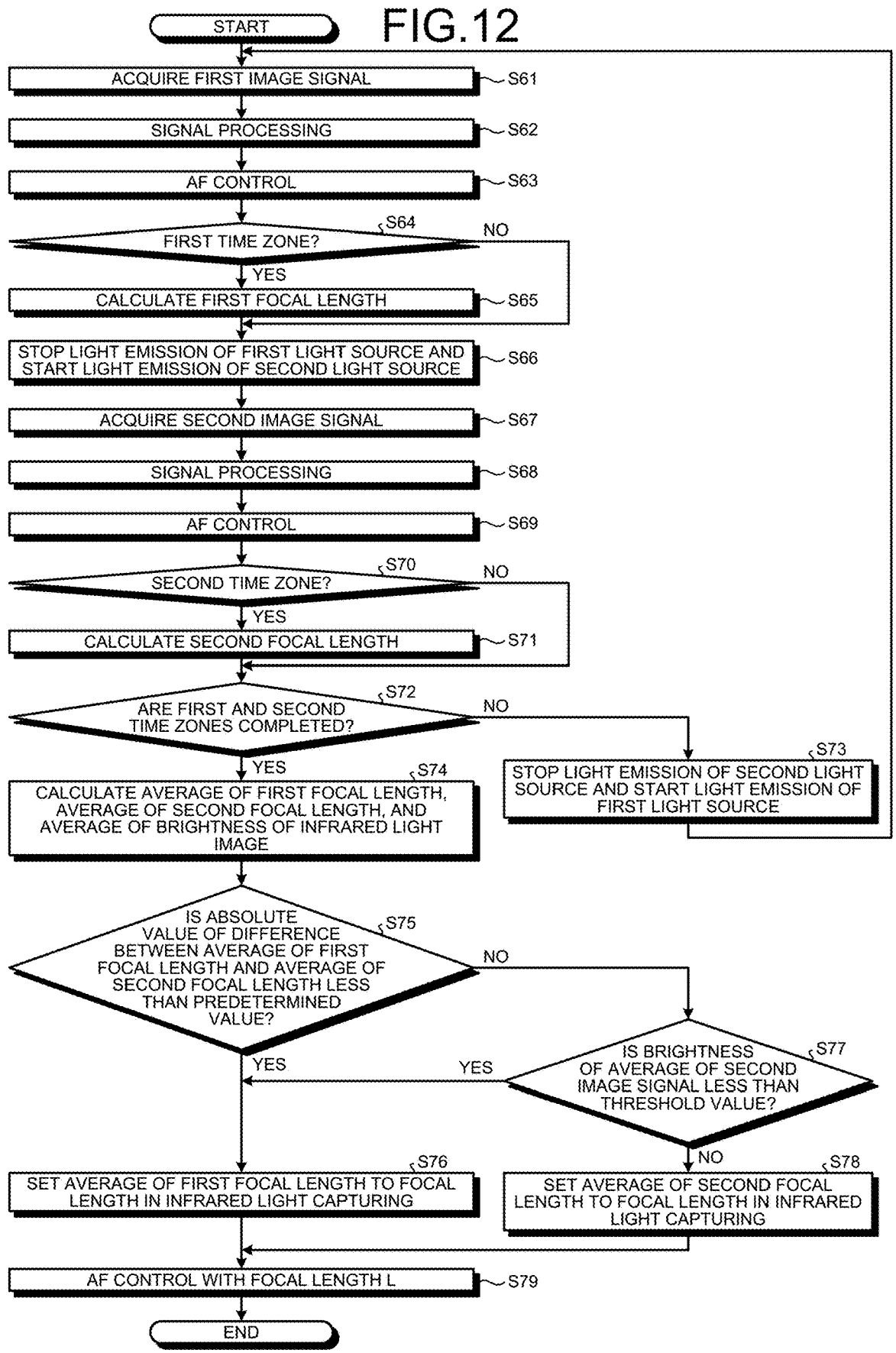
FIG. 12 is a flowchart illustrating the outline of the processing performed by the control device according to the fourth embodiment.

FIG. 12 is a flowchart illustrating an outline of the processing performed by the control device 5C, and is a flowchart illustrating an outline of the processing performed in a case where the input unit 46 receives an instruction for infrared light capturing, or in a case where the input unit 46 receives an AF activation instruction, or in a case where the movement of the imaging unit 44 is completed. In FIG. 12, it is assumed that the first light source 531 emits white light at the time of starting a series of processing (time $t_0$ in the case of the instruction of infrared light capturing illustrated in FIG. 11).

First, the processing of steps S61 to S63 sequentially corresponds to the processing of steps S1 to S3 described in the first embodiment.

After step S63, the control unit 55 determines whether or not the capturing time of the first image signal acquired in step S61 is included in the first time zone $\Delta T_1$ (step S64). As a result of the determination, if the capturing time of the first image signal is included in the first time zone $\Delta T_1$ (step S64: Yes), the AF controller 552 calculates the first focal length L1 (step S65).

Subsequent steps S66 to S69 correspond sequentially to steps S5 to S8 described in the first embodiment. As a result of the determination in step S64, if the capturing time of the first image signal is not included in the first time zone $\Delta T_1$ (step S64: No), the control device 5C shifts to step S66.

After step S69, the control unit 55 determines whether or not the capturing time of the second image signal acquired in step S67 is included in the second time zone $\Delta T_2$ (step S70). As a result of the determination, if the capturing time of the second image signal is included in the second time zone $\Delta T_2$ (step S70: Yes), the AF controller 552 calculates the second focal length L2 (step S71).

Subsequently, the AF controller 552 determines whether or not the first and second time zones are completed (step S72). As a result of the determination, if the first and second time zones are not completed (step S72: No), the light source controller 551 stops the light emission of the first light source 531 and starts the light emission of the second light source 532 (step S73). Thereafter, the control device 5C returns to step S61.

As a result of the determination in step S72, if the first and second time zones are completed (step S72: Yes), the AF controller 552 calculates an average <L1> of the first focal length L1 calculated so far, an average <L2> of the second focal length L2, and an average <B> of brightness B of infrared light image included in detection information (step S74).

Thereafter, the AF controller 552 sets the focal length for performing AF (steps S75 to S78). First, the AF controller 552 calculates an absolute value |<L1>-<L2>| of the difference between the average <L1> of the first focal length and the average <L2> of the second focal length, and compares the absolute value |<L1>-<L2>| with a predetermined value $\Delta L$ (step S75). As a result of the comparison, if |<L1>-<L2>|<$\Delta L$ (step S75: Yes), the AF controller 552 sets the average <L1> of the first focal length to the focal length L in infrared light capturing (step S76).

On the other hand, as a result of the comparison in step S75, if |<L1>-<L2>|≥$\Delta L$ (step S75: No), the AF controller 552 compares an average <B> of brightness of the R component in the detection frame of the second image signal with the threshold value Th (step S77). If <B><Th (step S77: Yes), the AF controller 552 shifts to step S76. On the other hand, if <B>≥Th (step S77: No), the AF controller 552 sets the average <L2> of the second focal length to the focal length L in infrared light capturing (step S78).

After step S76 or S78, the AF controller 552 performs AF control with the focal length L (step S79).

As a result of the determination in step S70, if the capturing time of the second image signal is not included in the second time zone $\Delta T_2$ (step S70: No), the control device 5C shifts to step S72.

Note that also in the fourth embodiment, in a case where the AF controller 552 sets the focal length, without performing the comparison processing (step S75) between the absolute value |<L1>-<L2>| of the difference between the average <L1> of the first focal length L1 and the average <L2> of the second focal length L2 and the predetermined value $\Delta L$, the average <B> of the brightness B in the detection frame of the second image signal may be compared with the threshold value Th, and the focal length L in infrared light capturing may be set according to the comparison result. In addition, a predetermined value in step S75 and a threshold value in step S77 do not have to be the same values as in the first embodiment.

According to the fourth embodiment described above, even in a case where white light and infrared light are alternately irradiated in a time-division manner, as in the third embodiment, focusing by autofocus may be appropriately performed regardless of the observation target, and the user may perform medical treatment by viewing an image with good visibility.

In addition, according to the fourth embodiment, since the first and second focal lengths are calculated separately for the first time zone for calculating the first focal length and the second time zone for calculating only the second focal length, this may be realized by a simple configuration.

Note that also in the fourth embodiment, as in the second embodiment described above, the control device may have a function of automatically or manually setting and changing the detection frame according to the image.

Other Embodiments

The embodiments for carrying out the present disclosure have been described above, but the present disclosure should not be limited only to the first to fourth embodiments described above. For example, the present disclosure may be applied to other special light observations. Examples of the specific other special light observation may include narrow band imaging (NBI) that radiates narrow-band illumination light with wavelengths of 415 nm and 540 nm as a center wavelength and uses a difference in absorption of light of each wavelength for hemoglobin to observe a state of blood vessels between a mucosal surface layer and a deeper layer, and auto fluorescence imaging (AFI) for diagnosing a tumor portion of the subject by pre-administering a fluorescent agent into the subject and radiating light obtained by combining blue excitation light (390 to 440 nm) with green light (540 to 560 nm) that is easily absorbed by hemoglobin.

In addition, the medical observation device according to the present disclosure may be an endoscope or an exoscope provided with the imaging device.

Note that the present technique may also have the following configurations.

(1) A control device including:

an acquisition unit configured to acquire first and second image signals generated by an imaging device having an autofocus function by capturing an observation target irradiated with first light and second light having different wavelength bands, respectively;

a signal processor configured to detect detection information of the first and second image signals; and a controller configured to calculate a first focal length based on the detection information of the first image signal, calculate a second focal length based on the detection information of the second image signal, and set a focal length of the imaging device to capture the observation target irradiated with the second light to either the first or second focal length at least based on the detection information of the second image signal.

(2) The control device according to (1), wherein the controller is configured to:

set a focal length for acquiring the second image signal to the first focal length in a case where an absolute value of a difference between the first focal length and the second focal length is smaller than a predetermined value; and set the focal length for acquiring the second image signal to either the first or second focal length according to a comparison result between a brightness of at least a part of a component of the second image signal and a threshold value in a case where the absolute value of the difference between the first focal length and the second focal length is equal to or greater than the predetermined value.

(3) The control device according to (1), wherein the controller is configured to set a focal length for acquiring the second image signal according to a comparison result between a brightness of at least a part of a component of the second image signal and a threshold value.

(4) The control device according to (2) or (3), wherein the controller is configured to:

set the focal length for acquiring the second image signal to the first focal length in a case where the brightness is smaller than the threshold value; and set the focal length for acquiring the second image signal to the second focal length in a case where the brightness is equal to or greater than the threshold value.

(5) The control device according to any one of (2) to (4), wherein the first light is white light and the second light is blue light, the first image signal is a signal of a white light image, and the second image signal is a signal of a fluorescence image containing red fluorescence emitted by a substance excited by the blue light, and the controller is configured to compare a brightness of a red component of the second image signal with a threshold value.

(6) The control device according to any one of (2) to (4), wherein the first light is white light and the second light is infrared light, the first image signal is a signal of a white light image, and the second image signal is a signal of a fluorescence image containing fluorescence emitted by a substance excited by the infrared light, and the controller is configured to compare a brightness of the second image signal with a threshold value.

(7) The control device according to (6), wherein the first and second image signals are signals generated by the imaging device in a case where the observation target is simultaneously irradiated with the first light and the second light.

(8) The control device according to (6), wherein the first and second image signals are signals generated by the imaging device in a case where the first light and the second light are alternately irradiated to the observation target in a time-division manner, and the controller is configured to calculate the first and second focal lengths by dividing into a first time zone in which only the first focal length is calculated by acquiring the first and second image signals, and a second time zone in which only the second focal length is calculated by acquiring the first and second image signals.

(9) The control device according to any one of (2) to (8), wherein the controller is configured to set a detection frame that defines a detection range of detection information in an image signal.

(10) The control device according to any one of (5) to (8), wherein the signal processor is configured to detect a fluorescence region where the fluorescence is emitted, and the controller is configured to set a detection frame that defines a detection range of detection information in an image signal according to a detection result of the fluorescence region.

(11) The control device according to any one of (1) to (10), wherein the controller is configured to cause a display device to display information indicating that the second image signal is being generated in a case where the imaging device is generating the second image signal.

(12) A medical observation system comprising:

an imaging device having an autofocus function and configured to generate an image signal by capturing an observation target; and a control device configured to process an image signal generated by the imaging device, the control device including an acquisition unit configured to acquire first and second image signals generated by imaging device by capturing an observation target irradiated with first light and second light having different wavelength bands, respectively;
a signal processor configured to detect detection information of the first and second image signals, and
a controller configured to
calculate a first focal length based on the detection information of the first image signal,
calculate a second focal length based on the detection information of the second image signal, and
set a focal length of the imaging device to capture the observation target irradiated with the second light to either the first or second focal length at least based on the detection information of the second image signal.

According to the present disclosure, the focusing by autofocus may be appropriately performed regardless of the observation target.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A control device comprising:
an acquisition circuit configured to receive first and second image signals generated by an imaging device having an autofocus function by capturing an observation target irradiated with first light and second light having different wavelength bands, respectively;
a signal processor configured to detect detection information of the first and second image signals; and
a control circuit configured to
calculate a first focal length based on the detection information of the first image signal,
calculate a second focal length based on the detection information of the second image signal,
determine a difference between the first focal length and the second focal length; and
set a focal length of the imaging device to capture the observation target irradiated with the second light to either the first or second focal length at least based on the difference.

2. The control device according to claim 1, wherein the control circuit is configured to:
set a focal length for acquiring the second image signal to the first focal length in a case where an absolute value of the difference is smaller than a predetermined value; and
set the focal length for acquiring the second image signal to either the first or second focal length according to a comparison result between a brightness of at least a part of a component of the second image signal and a threshold value in a case where the absolute value of the difference between the first focal length and the second focal length is equal to or greater than the predetermined value.

3. The control device according to claim 1, wherein the control circuit is configured to set a focal length for acquiring the second image signal according to a comparison result between a brightness of at least a part of a component of the second image signal and a threshold value.

4. The control device according to claim 2, wherein the control circuit is configured to:

set the focal length for acquiring the second image signal to the first focal length in a case where the brightness is smaller than the threshold value; and
set the focal length for acquiring the second image signal to the second focal length in a case where the brightness is equal to or greater than the threshold value.

5. The control device according to claim 2, wherein
the first light is white light and the second light is blue light,
the first image signal is a signal of a white light image, and the second image signal is a signal of a fluorescence image containing red fluorescence emitted by a substance excited by the blue light, and
the control circuit is configured to compare a brightness of a red component of the second image signal with a threshold value.

6. The control device according to claim 2, wherein
the first light is white light and the second light is infrared light,
the first image signal is a signal of a white light image, and the second image signal is a signal of a fluorescence image containing fluorescence emitted by a substance excited by the infrared light, and
the control circuit is configured to compare a brightness of the second image signal with a threshold value.

7. The control device according to claim 6, wherein the first and second image signals are signals generated by the imaging device in a case where the observation target is simultaneously irradiated with the first light and the second light.

8. The control device according to claim 6, wherein
the first and second image signals are signals generated by the imaging device in a case where the first light and the second light are alternately irradiated to the observation target in a time-division manner, and
the control circuit is configured to calculate the first and second focal lengths in a first time period in which only the first focal length is calculated by acquiring the first and second image signals based on the first image signals with in the first time period, and in a second time period in which only the second focal length is calculated by acquiring the first and second image signals based on the first image signals with in the first time period.

9. The control device according to claim 1, wherein the control circuit is configured to set a detection frame that defines a detection range of detection information in an image signal.

10. The control device according to claim 5, wherein
the signal processor is configured to detect a fluorescence region where the fluorescence image is present, and
the control circuit is configured to set a detection frame that defines a detection range of detection information in for the second image signal according to a detection result of the fluorescence region.

11. The control device according to claim 1, wherein the control circuit is configured to cause a display device to display information indicating that the second image signal is being generated in a case where the imaging device is generating the second image signal.

12. A medical observation system comprising:
an imaging device having an autofocus function and configured to generate an image signal by capturing an observation target; and
a control device configured to process an image signal generated by the imaging device, the control device including an acquisition circuit configured to acquire first and second image signals generated by the imaging device by capturing an observation target irradiated with first light and second light having different wavelength bands, respectively;

a signal processor configured to detect detection information of the first and second image signals, and a control circuit configured to calculate a first focal length based on the detection information of the first image signal, calculate a second focal length based on the detection information of the second image signal, determine a difference between the first focal length and the second focal length; and set a focal length of the imaging device to capture the observation target irradiated with the second light to either the first or second focal length at least based on the difference.

13. The medical observation system according to claim 12, wherein the control circuit is configured to set a focal length for acquiring the second image signal to the first focal length in a case where an absolute value of the difference is smaller than a predetermined value.

14. The medical observation system according to claim 13, wherein, in a case where the absolute value of the difference is equal to or greater than the predetermined value, the control circuit is configured to:

set the focal length for acquiring the second image signal to the first focal length in a case where a brightness of at least a part of a component of the second image signal is smaller than a threshold value; and set the focal length for acquiring the second image signal to the second focal length in a case where the brightness of at least the part of the component of the second image signal is equal to or greater than the threshold value.

15. The control device according to claim 8, wherein the control circuit is configured to calculate the first focal length by averaging first focal lengths acquired during the first time period and to calculate the second focal length by averaging second focal lengths acquired during the second time period.

16. The control device according to claim 10, wherein the control circuit is configured to set the detection frame such that a ratio of an area of the fluorescence region included in the detection frame to the area of the fluorescence region is equal to or greater than a predetermined threshold value.

17. A control circuit to control a focal length of an imaging device having an autofocus function that images an observation target irradiated with first light and second light having different wavelength bands, respectively, the control circuit configured to:

calculate a first focal length based on a first image signal of the observation target irradiated with the first light, calculate a second focal length based on a second image signal of the observation target irradiated with the second light, determine a difference between the first focal length and the second focal length; and set a focal length of the imaging device to capture the observation target irradiated with the second light to either the first or second focal length at least based on the difference.

18. The control circuit according to claim 17, further configured to set a focal length for acquiring the second image signal to the first focal length in a case where an absolute value of the difference is smaller than a predetermined value.

19. The control circuit according to claim 18, wherein, in a case where the absolute value of the difference is equal to or greater than the predetermined value, the control circuit is configured to:

set the focal length for acquiring the second image signal to the first focal length in a case where a brightness of at least a part of a component of the second image signal is smaller than a threshold value; and set the focal length for acquiring the second image signal to the second focal length in a case where the brightness of at least the part of the component of the second image signal is equal to or greater than the threshold value.

* * * * *